(12) United States Patent
Ohmstede

(10) Patent No.: US 6,626,891 B2
(45) Date of Patent: Sep. 30, 2003

(54) DRAINAGE SYSTEM TO BE USED WITH AN OPEN WOUND, AN ELEMENT WHICH IS USED THEREBY FOR PLACING A DRAINAGE TUBE OR HOSE, AND A METHOD OF USING SAID DRAINAGE SYSTEM

(75) Inventor: Volkert Simon Ohmstede, Neerpelt (BE)

(73) Assignee: Polymedics N.V., Peer (BE)

( * ) Notice: Subject to any disclaimer, the term of this patent is extended or adjusted under 35 U.S.C. 154(b) by 313 days.

(21) Appl. No.: 09/155,622

(22) PCT Filed: Jun. 30, 1998

(86) PCT No.: PCT/EP98/04041

§ 371 (c)(1),
(2), (4) Date: Apr. 15, 1999

(87) PCT Pub. No.: WO99/01173

PCT Pub. Date: Jan. 14, 1999

(65) Prior Publication Data

US 2002/0016577 A1 Feb. 7, 2002

(30) Foreign Application Priority Data

Jul. 3, 1997 (NL) ............................................. 1006457

(51) Int. Cl.[7] ............................................ A61M 27/00
(52) U.S. Cl. .................................................... 604/543
(58) Field of Search ................................. 604/313, 540, 604/27, 47, 543, 35, 36, 48, 73, 315, 316; 128/897; 602/42

(56) References Cited

U.S. PATENT DOCUMENTS

| | | | | |
|---|---|---|---|---|
| 2,122,121 A | 6/1938 | Elmer | | 128/350 |
| 3,572,340 A | 3/1971 | Lloyd | | 128/278 |
| 4,778,446 A | 10/1988 | Jensen | | 604/27 |
| 5,549,584 A | 8/1996 | Gross | | 604/313 |
| 5,636,643 A | * | 6/1997 | Argenta et al. | 128/897 |

FOREIGN PATENT DOCUMENTS

| | | |
|---|---|---|
| EP | 0 620 720 B1 | 10/1994 |
| WO | 94 20041 | 9/1994 |

* cited by examiner

*Primary Examiner*—Weilun Lo
*Assistant Examiner*—Michele Kidwell
(74) *Attorney, Agent, or Firm*—Ladas & Parry

(57) ABSTRACT

The invention relates to a drainage system to be used with an open wound, which system consists of a block of a porous, moisture absorbing material, which is connected to a tube or hose, which is in turn connected to a suction unit, which porous material is covered with a foil, wherein an element consisting of a plate-shaped member is provided on the porous, moisture absorbing material, the plate-shaped member being provided on the upper side with a partially open thickening for placing or inserting the tube or hose, which thickening is provided on the underside with one or more openings, which open into and cooperate with openings in the plate shaped member. The invention furthermore relates to the element and to a method of using the drainage system.

2 Claims, 2 Drawing Sheets

DRAINAGE SYSTEM TO BE USED WITH AN OPEN WOUND, AN ELEMENT WHICH IS USED THEREBY FOR PLACING A DRAINAGE TUBE OR HOSE, AND A METHOD OF USING SAID DRAINAGE SYSTEM

BACKGROUND OF THE INVENTION

The invention relates to a drainage system to be used with an open wound, which system consists of a block of a porous, moisture-absorbing material, which is connected to a tube or hose, which is in turn connected to a suction unit, which porous material is covered with a foil. The invention furthermore relates to an element for placing a drainage tube or hose, and to a method of using the drainage system.

A drainage system of this kind is known from EP-A-0 620 720. According to said European patent application, a drainage system as shown in FIG. 1 is used. A foam block is thereby placed in the open wound, the foam block, which absorbs the wound fluid, is connected to a suction hose, and the whole consisting of the wound, the foam block and a part of the suction hose is covered with a foil. In this way wound fluid is withdrawn. In practice this known system has a few drawbacks, among other things because the covering of the whole consisting of the wound, the foam block and the suction hose connected thereto with the foil is problematic.

That is why attempts have been made to find an improved drainage system, and this has been accomplished by using a drainage system according to the invention. Said new drainage system is characterized in that an element consisting of a plate-shaped member is provided on the porous, moisture-absorbing material, said plate-shaped member being provided on the upper side with a partially open thickening for placing or inserting the tube or hose therein, which thickening is provided on the underside with one or more openings, which open into and cooperate with openings in the plate-shaped member. Furthermore, the foil is preferably affixed to the plate-shaped member, whereby said thickening is not covered.

From EP-A-0 688 189 (which corresponds with WO 94/20041 in the name of the proprietor of EP-A-0 620 720) two wound treatment systems are known which work at a reduced pressure, whereby the system as described in FIG. 1 of EP-A-0 688 189 is an improvement in comparison with the drainage system as described in EP-A-0 620 720. The improvement consists of the fact that suction tube 12 is inserted into foam block 10, which tube 12a is provided with one or more openings 14, which function to enable the withdrawal of wound fluid via hose 12. The improvement in accordance with the present invention consists of the fact that when the element according to the invention is used, the suction tube does not need be inserted into the foam block which absorbs the wound fluid, but only needs to be connected to the open thickening which is present on the element. Furthermore, the foil can be easily affixed to the element according to the invention, without any risk of the foil coming into contact with the wound. The second embodiment according to EP-A-0 688 189 is shown in FIG. 5 of the said European patent application. According to said FIG. 5, a bell-shaped member provided with openings and with a suction tube is placed on a foam pad 120 which is present in the wound. A foil is draped over said bell-shaped member, which foil is drawn tighter against said bell-shaped member when a reduced pressure is applied. The edges of the wound will be pulled inwardly under the influence of said reduced pressure, so that the wound will heal more quickly. The result of the application of said reduced pressure, however, is that no wound fluid is withdrawn via said foam pad and the hose which connects the reduced pressure source and the bell-shaped member. Accordingly, the embodiment as shown in FIG. 5 of EP-A-0 688 189 is different as regards design and purpose from the drainage system and the associated element according to the present invention.

The above embodiment as shown in FIG. 5 of EP-A-0 688 189 is comparable with the drainage system which is described in U.S. Pat. No. 2,122,121 (1938). The drainage system known from U.S. Pat. No. 2,122,121 is in particular intended for treating wounds resulting from urinary bladder operations. Accordingly, the drainage system is provided round the upper legs by means of bands 43 (FIG. 1 of said U.S. patent) and placed on the lower abdomen. A gauze package 40 is placed in the bell-shaped member 1 as shown in FIG. 4, which gauze package is screened by a perforated raised portion 16. Air is drawn in via said perforations and a ring line, and sucked out via pipe 30. The pieces of gauze that have absorbed wound fluid can be substituted for clean ones every day. The purpose of the system according to said U.S. patent is to effect an air circulation over the wound, whereby wound fluid is absorbed in the pieces of gauze, which wound fluid is not withdrawn via the vacuum system, however, but which remains present in said pieces of gauze. This in contrast to the system and the element according to the invention.

U.S. Pat. Nos. 3,572,340; 4,778,446 and 5,549,584 do not describe an element according to the present invention, nor do they describe the use of said element in a drainage system according to the present invention, therefore.

The element which can be used in the drainage system according to the invention is characterized in that it consists of a plate-shaped member, on which a partially open thickening is present, for applying or inserting a tube or a hose, which thickening is provided with one or more openings on the underside, which openings are in communication with the openings through the plate-shaped member. The openings through the plate-shaped member preferably continue into the thickening. The thickening is preferably closed at one end and open at the other end, so that a hose or a tube can be inserted into or applied on said open end.

BRIEF SUMMARY OF THE INVENTION

The drainage system according to the invention is used for treating a chronic or acute wound by placing the porous block or a spongy, liquid-absorbing material made of a microporous foam on the wound. Then the element according to the invention is provided on the porous block, and the whole is covered with a foil, whereby the thickening on the element remains freely accessible for the tube or hose which is place or inserted into or applied on the open end of said thickening. After the foil has been adhesively provided on the skin surrounding the wound, a reduced pressure can be applied under the foil, so that wound fluid can be withdrawn.

BRIEF DESCRIPTION OF THE DRAWINGS

The invention will be explained in more detail in the description below, wherein reference is made to the appended drawing, wherein.

DETAILED DESCRIPTION OF THE INVENTION

Figure 1:
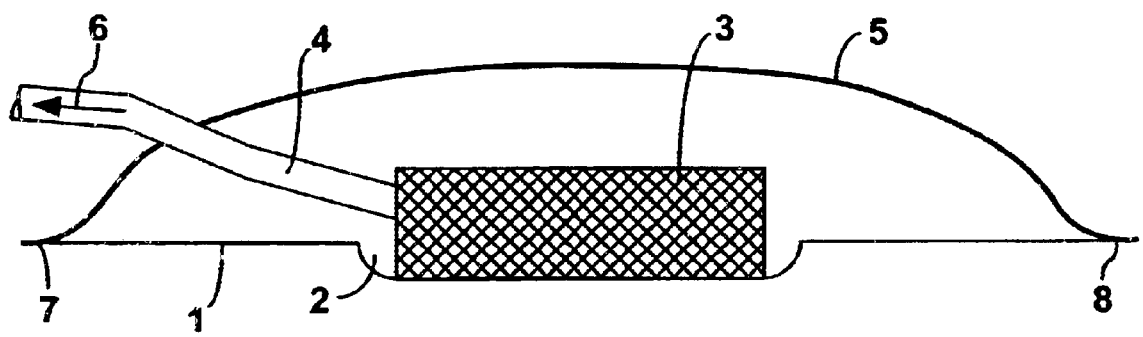
FIG. 1 shows the drainage system known from EP-A-0 620 720.

FIG. 1 shows the known drainage system, wherein a wound 2 is present in skin 1. A block of a porous or foamy material 3 is placed on wound 2, which block is capable of absorbing wound fluid. A hose 4 is connected to porous material 3, which hose,is connected to a suction pump. The direction of suction is indicated by arrow 6. The whole consisting of wound 2, block 3 and a part of hose 4 is covered with a foil 5, which is adhesively provided on the skin at points 7 and 8, so that a reduced pressure can be applied within the envelope formed by skin 1 and foil 5.

Figure 2:
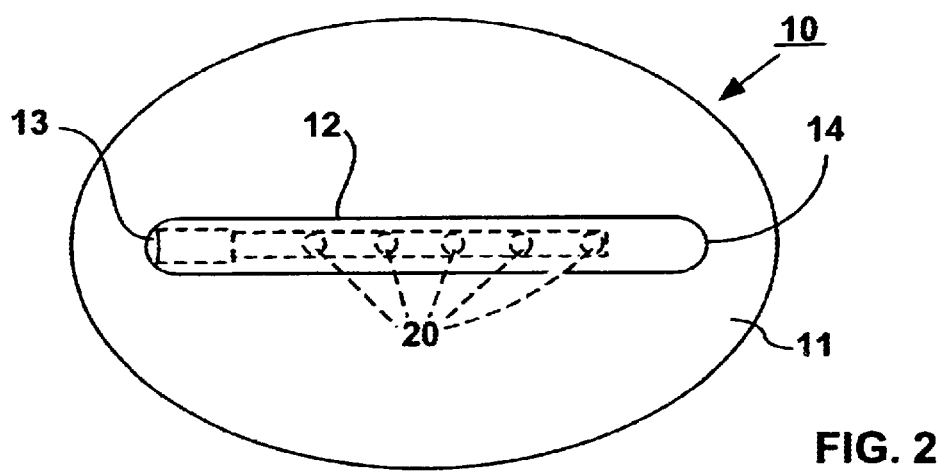
FIG. 2 shows the upper side of the element which is used in the drainage system according to the invention.

FIG. 2 shows the upper side of element 10, which consists of a plate-shaped member 11 with the thickening 12 present thereon. Thickening 12 is open at one end 13, and closed at the other end 14. A tube can be inserted into the hollow thickening via opening 13, or a hose having the function of hose 4 in FIG. 1 can be connected thereto. The foil indicated at 5 in FIG. 1 may be affixed to plate-shaped member 11, so that said element and said foil are in one piece.

Figure 3:
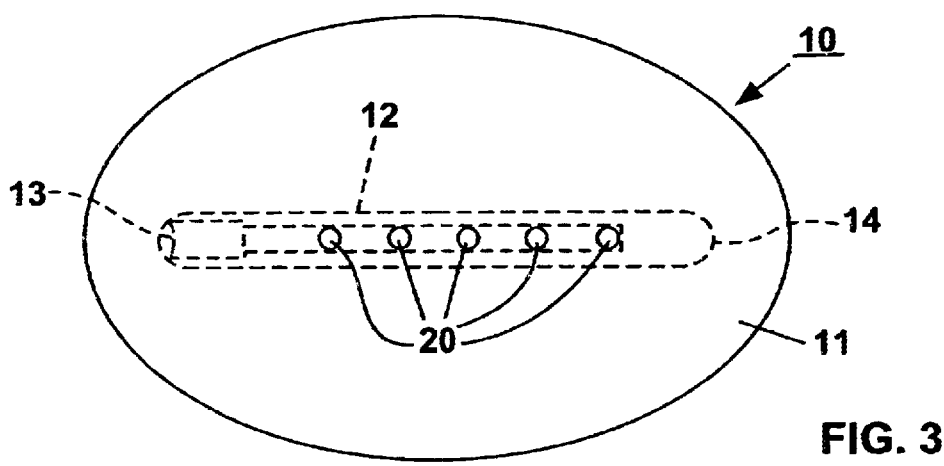
FIG. 3 shows the underside of the element which is used in the drainage system according to the invention.

FIG. 3 shows the bottom side of element 10, which consists of plate-shaped member 11 and the circumference of thickening 12. Openings 20 are present in the underside of plate-shaped member 11, which openings continue into thickening 12.

The underside of element 10 may be present on top of the block of porous material, whilst the foil may be provided on the upper side of said element, so that these three parts, which are essential for the proper functioning of the drainage system according to the invention may be integral with each other. This means a simplification of the method for using the drainage system, thus minimising the occurrence of mistakes in using a drainage system according to the invention.

Figure 4:
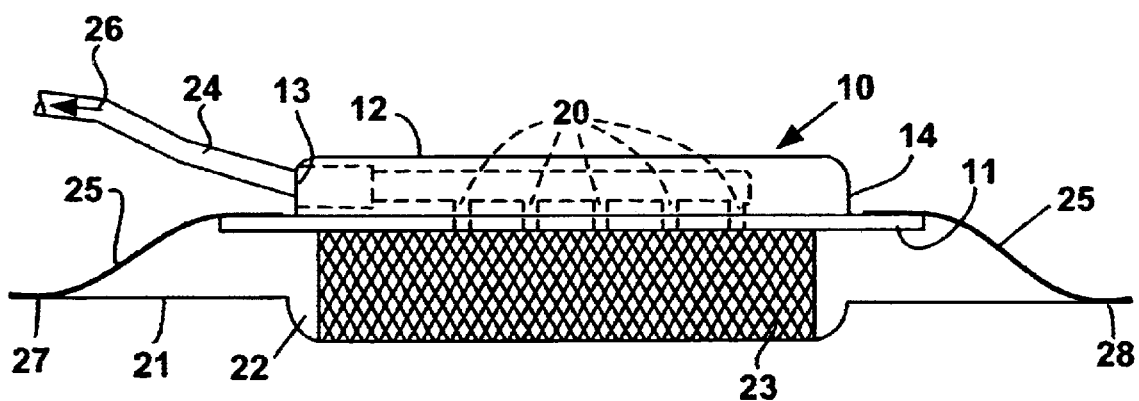
FIG. 4 diagrammatically shows the use of the drainage system according to the invention.

FIG. 4 diagrammatically shows the use of the drainage system according to the invention. FIG. 4 shows an open wound 22 in skin 21 (the numerals correspond with those in FIG. 1), in which wound a block 23 of a foamy material is present. Examples of said foamy material are polyvinyl alcohol and polyurethane. Present on block 23 is element 10, which consists of plate-shaped member 11 comprising thickening 12. Thickening 12 is provided with open end 13 and closed end 14. Openings 20 are provided through plate-shaped member 11, which openings open into the hollow space within thickening 12. Foil 25 is affixed to the upper side of plate-shaped member 11, which foil is also adhesively provided on skin 21, at points 27 and 28. The hose or tube 24 is inserted into the open end 13 of thickening 12 and connected to suction unit 26. It will be apparent that the construction according to FIG. 4 is much simpler to provide and safer to use, and that it provides a better seal on the skin and round the hose than the drainage system as shown in FIG. 1.

Projections, guide ribs and the like may be provided on the underside of the element so as to provide a better guidance for the fluid from the upper side of the block of porous material to the openings present under the thickening. It is preferred to use a foil as described in Dutch patent application No. 1,005,726, which is marketed under the brand name Simpatex (Akzo).

In the simplest embodiment of the invention, the element is provided on the underside with a porous material, such as a spongy material of polyvinyl alcohol, and Simpatex (brand name) is affixed to the upper side of the element. Then the spongy material, on which the element and the foil are provided, is placed on the wound, and the foil is adhesively provided on the skin surrounding the wound. Then a hose is inserted into the thickening, and the hose is connected to a vacuum pump. Thus, a reduced pressure can be applied under the foil, and the wound fluid can be withdrawn.

What is claimed is:

1. A component for use with an open wound drainage system, said drainage system comprising a block of a porous, moisture-absorbing material, said component comprising a plate-shaped member having an upper side and an underside, and a partially open hollow thickening member, said thickening member being directly disposed on said upper side of said plate-shaped member, said component being disposed on said block, said block being connected to a tube or to a hose via said partially open hollow thickening member through which a suction force may be applied to said tube or hose, wherein said thickening is closed at one end and open at the other end, so that a hose or a tube can be inserted into or applied on said open end.

2. A component for use with an open wound drainage system, said drainage system comprising a block of a porous, moisture-absorbing material, said component comprising a plate-shaped member having an upper side and an underside, and a partially open hollow thickening member, said thickening member being directly disposed on said upper side of said plate-shaped member, said component being disposed on said block, said block being connected to a tube or to a hose via said partially open hollow thickening member through which a suction force may be applied to said tube or hose, wherein projections are provided on said underside of said plate-shaped element, said projections guiding fluids emanating from said block of the porous material to said openings of said thickening.

* * * * *